United States Patent
Sasaki

(10) Patent No.: US 12,242,004 B2
(45) Date of Patent: Mar. 4, 2025

(54) RADIATION IMAGING SYSTEM, RADIATION CONTROL APPARATUS, CONTROL METHOD OF RADIATION IMAGING SYSTEM, CONTROL METHOD OF RADIATION CONTROL APPARATUS, AND NON-TRANSITORY COMPUTER-READABLE STORAGE MEDIUM

(71) Applicant: CANON KABUSHIKI KAISHA, Tokyo (JP)

(72) Inventor: Hiroshi Sasaki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 225 days.

(21) Appl. No.: 18/047,987

(22) Filed: Oct. 19, 2022

(65) Prior Publication Data
US 2023/0126864 A1    Apr. 27, 2023

(30) Foreign Application Priority Data
Oct. 21, 2021    (JP) .................................. 2021-172654

(51) Int. Cl.
*G01T 1/17*    (2006.01)
*A61B 6/00*    (2024.01)

(52) U.S. Cl.
CPC ................. *G01T 1/17* (2013.01); *A61B 6/542* (2013.01)

(58) Field of Classification Search
CPC ............ G01T 1/17; A61B 6/542; A61B 6/548
See application file for complete search history.

(56) References Cited

U.S. PATENT DOCUMENTS

2022/0401054 A1* 12/2022 Taya .................... A61B 6/4035

FOREIGN PATENT DOCUMENTS

| CN | 112738391 A | 4/2021 | |
|---|---|---|---|
| JP | 2017202034 A | 11/2017 | |
| JP | 7441203 B2 * | 2/2024 | ............. A61B 6/542 |

OTHER PUBLICATIONS

European Patent Office, Extended European Search Report for Application No. 22201923.4, Mar. 2023.

* cited by examiner

*Primary Examiner* — David P Porta
*Assistant Examiner* — Gisselle M Gutierrez
(74) *Attorney, Agent, or Firm* — Canon U.S.A., Inc. IP Division

(57) ABSTRACT

A radiation imaging system comprising a radiation imaging apparatus configured to detect radiation emitted from a radiation source, and a radiation control apparatus configured to control the radiation source is provided. The radiation imaging apparatus is configured to output dose information, which includes a dose of radiation entering the radiation imaging apparatus and a time at which the dose was detected, to the radiation control apparatus a plurality of times. The radiation control apparatus is configured to set the threshold dose based on a difference between a time included in the dose information from the radiation imaging apparatus and a time at which the radiation control apparatus received the dose information, and control the radiation source to stop radiation irradiation based on the threshold dose.

20 Claims, 9 Drawing Sheets

RADIATION IMAGING SYSTEM, RADIATION CONTROL APPARATUS, CONTROL METHOD OF RADIATION IMAGING SYSTEM, CONTROL METHOD OF RADIATION CONTROL APPARATUS, AND NON-TRANSITORY COMPUTER-READABLE STORAGE MEDIUM

BACKGROUND

Field of the Disclosure

The present disclosure relates to a radiation imaging system, a radiation control apparatus, a control method of the radiation imaging system, a control method of the radiation control apparatus, and a non-transitory computer-readable storage medium.

Description of the Related Art

In medical image diagnosis and nondestructive inspection, a radiation imaging apparatus using a sensor which detects radiation has been broadly used. Such a radiation imaging apparatus is known to monitor radiation entering the radiation imaging apparatus and detect the start and end of radiation irradiation and the integrated irradiation amount of radiation. Japanese Patent Laid-Open No. 2017-202034 describes a radiation imaging system in which a radiation control apparatus for controlling radiation irradiation controls the timing of stopping radiation irradiation based on arrival dose information including an arrival dose output from a radiation imaging apparatus and information of the time at which the arrival dose was acquired.

SUMMARY

The time required for the radiation control apparatus to acquire the arrival dose information output from the radiation imaging apparatus can fluctuate due to a communication delay caused by external noise or the like. The fluctuation of the time required for the radiation control apparatus to acquire the arrival dose information can affect control of radiation irradiation.

Some embodiments of the present disclosure provide a technique advantageous in control of radiation irradiation.

According to some embodiments, a radiation imaging system comprising a radiation imaging apparatus configured to detect radiation emitted from a radiation source, and a radiation control apparatus configured to control the radiation source is provided. The radiation imaging apparatus may output dose information, which includes a dose of radiation entering the radiation imaging apparatus and a time at which the dose was detected, to the radiation control apparatus a plurality of times. The radiation control apparatus may set the threshold dose based on a difference between a time included in the dose information from the radiation imaging apparatus and a time at which the radiation control apparatus received the dose information, and may control the radiation source to stop radiation irradiation based on the threshold dose.

According to some other embodiments, a radiation control apparatus that controls a radiation source configured to emit radiation to a radiation imaging apparatus is provided. The radiation control apparatus may set the threshold dose based on a difference between a time included in the dose information from the radiation imaging apparatus and a time at which the radiation control apparatus received the dose information, and may control the radiation source to stop radiation irradiation based on the threshold dose.

According to still other embodiments, a control method of a radiation imaging system comprising a radiation imaging apparatus configured to detect radiation emitted from a radiation source, and a radiation control apparatus configured to control the radiation source is provided. The method may comprise causing the radiation imaging apparatus to output dose information, which includes a dose of radiation entering the radiation imaging apparatus and a time at which the dose was detected, to the radiation control apparatus; causing the radiation control apparatus to set the threshold dose based on a difference between a time included in the dose information from the radiation imaging apparatus and a time at which the radiation control apparatus received the dose information; and causing the radiation control apparatus to control the radiation source to stop radiation irradiation based on the threshold dose.

According to yet other embodiments, a control method of a radiation control apparatus that controls a radiation source configured to emit radiation to a radiation imaging apparatus is provided. The method may comprise setting the threshold dose based on a difference between a time included in the dose information from the radiation imaging apparatus and a time at which the radiation control apparatus acquired the dose information; and controlling the radiation source to stop radiation irradiation based on the threshold dose.

According to further embodiments, a non-transitory computer-readable storage medium storing a program for causing a computer to execute a control method of a radiation imaging system comprising a radiation imaging apparatus configured to detect radiation emitted from a radiation source, and a radiation control apparatus configured to control the radiation source is provided. The method may comprise causing the radiation imaging apparatus to output dose information, which includes a dose of radiation entering the radiation imaging apparatus and a time at which the dose was detected, to the radiation control apparatus; causing the radiation control apparatus to set the threshold dose based on a difference between a time included in the dose information from the radiation imaging apparatus and a time at which the radiation control apparatus received the dose information; and causing the radiation control apparatus to control the radiation source to stop radiation irradiation based on the threshold dose.

According to still further embodiments, a non-transitory computer-readable storage medium storing a program for causing a computer to execute a control method of a radiation control apparatus that controls a radiation source configured to emit radiation to a radiation imaging apparatus is provided. The method may comprise setting the threshold dose based on a difference between a time included in the dose information from the radiation imaging apparatus and a time at which the radiation control apparatus acquired the dose information; and controlling the radiation source to stop radiation irradiation based on the threshold dose.

The radiation control apparatus may specify, based on the dose information, a threshold time at which an arrival dose entering the radiation imaging apparatus reaches the threshold dose. The radiation control apparatus may set the threshold dose based on a difference between a time included in one piece of dose information among a plurality of pieces of the dose information and a time at which the radiation control apparatus acquired the one piece of dose information. The radiation control apparatus may set the threshold dose based on differences between times included in two or more pieces of dose information among a plurality of pieces of the dose information and times at which the radiation control apparatus acquired the two or more pieces of dose information, respectively. If the difference exceeds a predetermined threshold, the radiation control apparatus may set the threshold dose. The radiation control apparatus may set the threshold dose based on dose information, among a plurality of pieces of the dose information, acquired at a preset timing.

The radiation control apparatus may set the threshold dose based on dose information, among a plurality of pieces of the dose information, acquired at a timing at which a predetermined period has elapsed since the threshold dose was last changed. If the arrival dose reaches the threshold dose or if a time reaches the threshold time, the radiation control apparatus may control the radiation source to stop radiation irradiation. Based on the dose information and the threshold time, the radiation control apparatus may transmit a signal which causes the radiation source to stop radiation irradiation. Based on a time from when the signal is transmitted to when the radiation source stops radiation irradiation, the radiation control apparatus may set at least one of the threshold dose or the threshold time.

The radiation control apparatus and the radiation source may be configured to capable of communication by wired communication. The radiation imaging apparatus and the radiation control apparatus may be configured to capable of communication by wireless communication.

The system may include a synchronizer configured to synchronize a time of the radiation imaging apparatus and a time of the radiation control apparatus. The synchronizer may be configured to synchronize the time of the radiation imaging apparatus and the time of the radiation control apparatus by wired communication or wireless communication. The synchronizer may synchronize the time of the radiation imaging apparatus and the time of the radiation control apparatus before radiation is emitted. The synchronizer may set the time of the radiation imaging apparatus based on the time of the radiation control apparatus.

Further features of various embodiments will become apparent from the following description of exemplary embodiments (with reference to the attached drawings).

DESCRIPTION OF THE EMBODIMENTS

Figure 1:
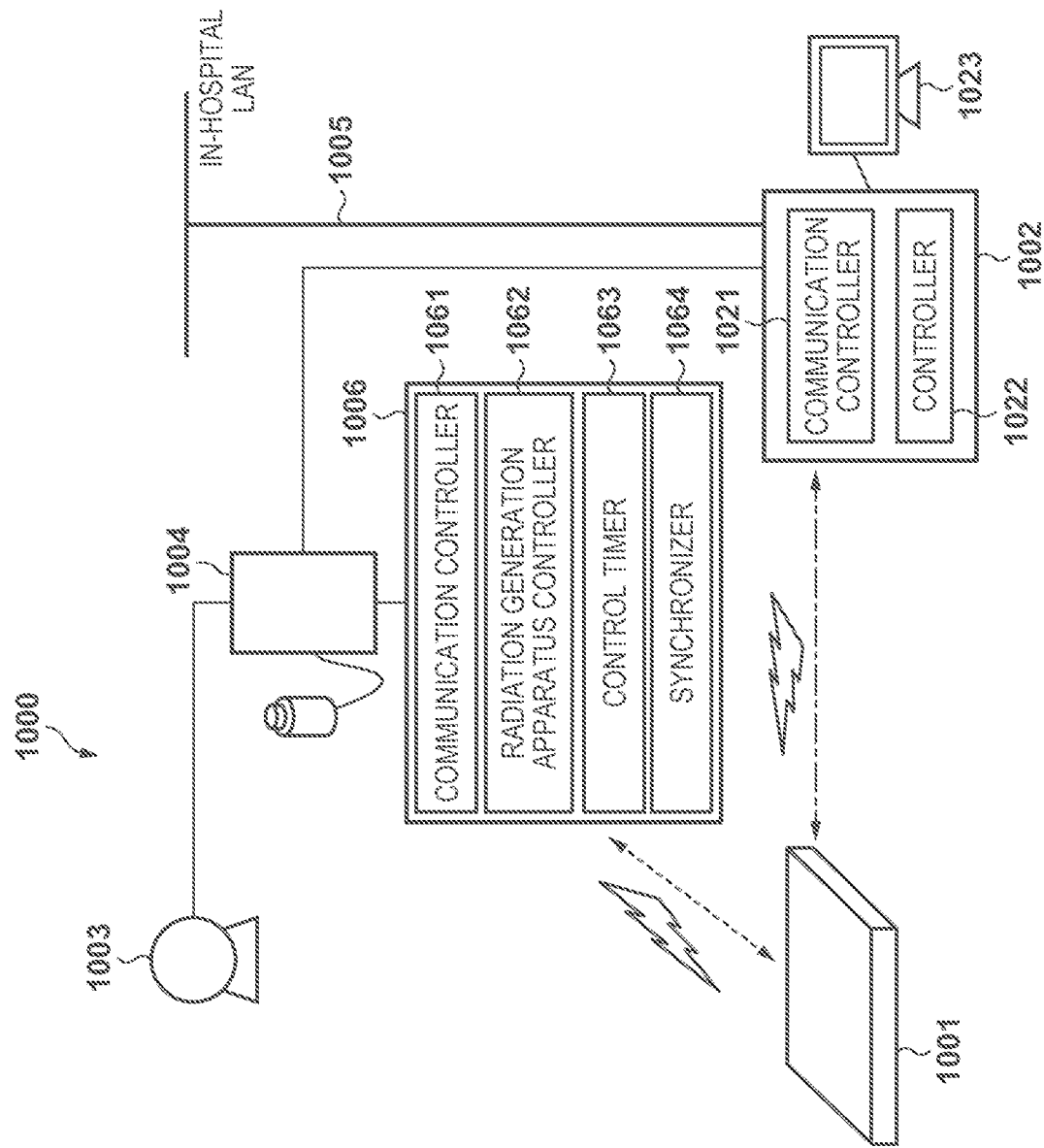
FIG. 1 is a view showing a configuration example of a radiation imaging system according to an embodiment.

Hereinafter, embodiments will be described in detail with reference to the attached drawings. Note, the following embodiments are not intended to limit the scope of every embodiment. Multiple features are described in the embodiments, but limitation is not made to embodiments that require all such features, and multiple such features may be combined as appropriate. Furthermore, in the attached drawings, the same reference numerals are given to the same or similar configurations, and redundant description thereof is omitted.

Radiation in the present disclosure can include α-rays, β-rays, γ-rays, and the like, which are beams generated by particles (including photons) emitted by radiation decay, as well as beams having the similar or higher energy, for example, X-rays, particle beams, cosmic rays, and the like.

With reference to FIGS. 1 to 9, the configuration and operation of a radiation imaging system according to an embodiment will be described. FIG. 1 shows a configuration example of a radiation imaging system 1000 according to this embodiment. The radiation imaging system 1000 is used, for example, when capturing a radiation image in a hospital, and includes a radiation imaging apparatus 1001, a control apparatus 1002, a radiation source 1003, a radiation source control apparatus 1004, a LAN 1005 (in-hospital LAN), and a radiation control apparatus 1006 as its functional components.

The radiation imaging apparatus 1001 detects radiation emitted from the radiation source 1003 and transmitted through a subject. A radiation image is captured based on the radiation detected by the radiation imaging apparatus 1001. The control apparatus 1002 includes, as functional components, a communication controller 1021 that controls communication, and a controller 1022 that controls an overall operation of the control apparatus 1002. For example, the controller 1022 of the control apparatus 1002 generates setting information for setting an image condition, setting operation control, and the like with respect to the radiation imaging apparatus 1001. And the communication controller 1021 of the control apparatus 1002 transmits, to the radiation imaging apparatus 1001, the setting information for setting the imaging condition, setting the operation control, and the like.

The radiation imaging apparatus 1001 transmits, for example, information of an image captured based on the set imaging condition setting, operation control setting, and the like, the arrival dose, and the like to the control apparatus 1002. For example, the control apparatus 1002 can use a mouse and a keyboard as input devices and can use a display 1023 or the like as an output device to allow input and output of information, such as the imaging condition setting, operation control setting, and the like.

The radiation source 1003 includes, for example, a rotor and a radiation tube that accelerates electrons by a high voltage and collides them against an anode to generate radiation. The radiation emitted from the radiation source 1003 is applied to the subject. The radiation imaging apparatus 1001 detects the radiation transmitted through the subject and generates a signal for forming a radiation image.

The radiation control apparatus 1006 acquires dose information output from the radiation imaging apparatus 1001, which includes the dose of radiation entering the radiation imaging apparatus 1001, and information (timer information) of the time measured by a sensor timer 228 of the radiation imaging apparatus 1001. Although details will be described later, based on information such as the dose information, the radiation control apparatus 1006 outputs, to the radiation source control apparatus 1004, an irradiation control signal for controlling radiation irradiation via the radiation source 1003.

Figure 2:
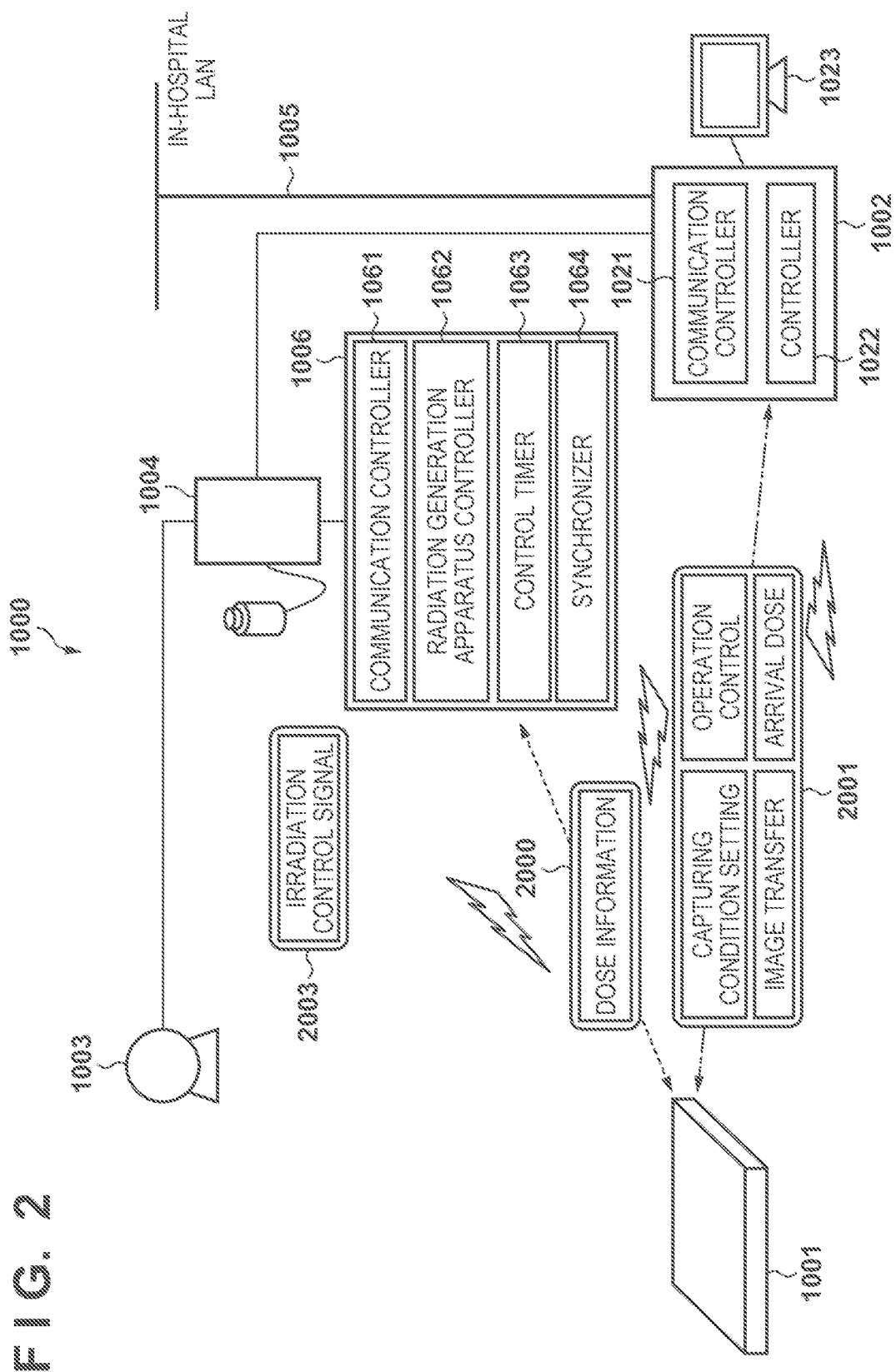
FIG. 2 is a view showing an example of data communication in the radiation imaging system shown in FIG. 1.

FIG. 2 is a view showing an example of data communication between respective apparatuses of the radiation imaging system 1000. The radiation imaging apparatus 1001 can include, for example, two communication units, such as a wireless communication unit and a wired communication unit. The radiation imaging apparatus 1001 is configured to be capable of communication with the communication controller 1021 of the control apparatus 1002 and a communication controller 1061 of the radiation control apparatus 1006 by using the two communication units. In data communication 2001 between the control apparatus 1002 and the radiation imaging apparatus 1001, information, such as the imaging condition setting, the operation control setting, transfer of image information, and the arrival dose, are transmitted. In data communication 2000 between the radiation control apparatus 1006 and the radiation imaging apparatus 1001, the above-described dose information including information of the dose entering the radiation imaging apparatus 1001 and information of the time at which the dose was detected, and the like, are transmitted. In the data communication 2000, the radiation imaging apparatus 1001 may be configured to be capable of communication with the communication controller 1061 of the radiation control apparatus 1006 by using the wireless communication unit. The radiation control apparatus 1006 outputs information, such as an irradiation control signal, to the radiation source control apparatus 1004 based on the acquired dose information. That is, the irradiation control signal and the like are transmitted in data communication 2003 between the radiation control apparatus 1006 and the radiation source control apparatus 1004. In the data communication shown in FIG. 2, the dose information indicates the dose which was emitted from the radiation source 1003 to the radiation imaging apparatus 1001 and arrived at the radiation imaging apparatus 1001.

The irradiation control signal transmitted from the radiation control apparatus 1006 to the radiation source control apparatus 1004 can include two signals of a stop signal (irradiation-stop signal) for stopping radiation irradiation and an irradiation signal (non-irradiation-stop signal) for causing radiation irradiation. By controlling output of both or one of the stop signal and the irradiation signal, the radiation control apparatus 1006 can control irradiation and the stopping of irradiation from the radiation source 1003 via the radiation source control apparatus 1004.

For example, as an example of controlling the output of one of the stop signal and the irradiation signal, the radiation control apparatus 1006 outputs the irradiation signal during radiation irradiation, and the radiation control apparatus 1006 stops output of the irradiation signal when stopping the radiation irradiation. Also, for example, the radiation control apparatus 1006 may stop output of the stop signal during radiation irradiation, and the radiation control apparatus 1006 may output the stop signal when stopping the radiation irradiation. In this manner, by switching between outputting and stopping the outputting of the irradiation signal or the stop signal, the radiation control apparatus 1006 can control irradiation of radiation or the stopping of irradiation of radiation in the radiation source control apparatus 1004.

As an example of controlling the output of both of the irradiation signal and the stop signal, the radiation control apparatus 1006 outputs the irradiation signal and stops output of the stop signal to the radiation source control apparatus 1004 during radiation irradiation. When stopping the radiation irradiation, the radiation control apparatus 1006 stops the output of the irradiation signal and outputs the stop signal to the radiation source control apparatus 1004. In this manner, by switching output operations of both the irradiation signal and the stop signal, the radiation control apparatus 1006 can control irradiation of radiation or control the stopping of irradiation of radiation in the radiation source 1003 via the radiation source control apparatus 1004.

The wired communication unit, which is included in the radiation imaging apparatus 1001 as a component for performing communication, is an information transmission path, and allows communication of information by, for example, a cable connection using a communication standard having a predetermined rule or a standard, such as RS232C, USB, or Ethernet®. The wireless communication unit, which is included in the radiation imaging apparatus 1001 as a component for performing communication, is also an information transmission path, and includes, for example, a circuit board including a communication IC and the like. The wireless communication unit is electrically connected to an antenna (not shown), and performs communication using a radio wave. The circuit board including the communication IC and the like can perform protocol communication processing based on a wireless LAN via the antenna. The frequency band, standard, and method of the wireless communication are not particularly limited, and a short-range wireless method such as NFC (Near field radio communication) or Bluetooth®, or a method such as UWB (Ultra Wide band) may be used. In addition, the wireless communication unit may be configured to be capable of communication using a plurality of wireless communication methods, and an appropriate method may be selected, as appropriate, to perform communication.

Figure 3:
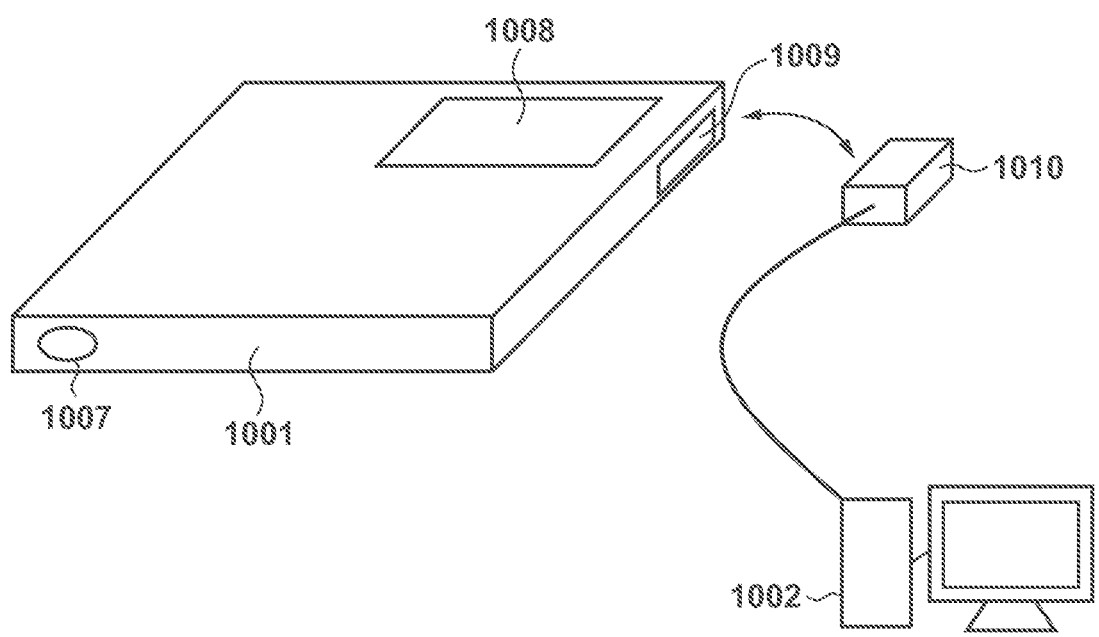
FIG. 3 is a view showing an example of the outer appearance of a radiation imaging apparatus used in the radiation imaging system shown in FIG. 1.

The radiation imaging apparatus 1001 may be, for example, a portable cassette flat panel detector (FPD). FIG. 3 is a view exemplarily showing the outer appearance of the portable radiation imaging apparatus 1001. The radiation imaging apparatus 1001 can include a power button 1007 for accepting power-on or power-off, a battery unit 1008 for power supply, and a connector connection unit 1009. The battery unit 1008 may be configured to be detachable. The battery main body included in the battery unit 1008 is configured to be chargeable by a battery charger (charging device) or the like.

The radiation imaging apparatus 1001 can be connected to the control apparatus 1002 using a cable 1010, and the cable 1010 can be connected to the radiation imaging apparatus 1001 via the connector connection unit 1009. When the radiation imaging apparatus 1001 and the control apparatus 1002 are connected using the cable 1010, for example, the radiation imaging apparatus 1001 is switched to communication using the wired communication unit. In accordance with this, information transmission between the radiation imaging apparatus 1001 and the control apparatus 1002 as shown in FIG. 2 is performed by wired communication. Further, the communication unit used in the radiation imaging apparatus 1001 may be switchable from the control apparatus 1002 by a user operation regardless of the connection form.

Figure 4:
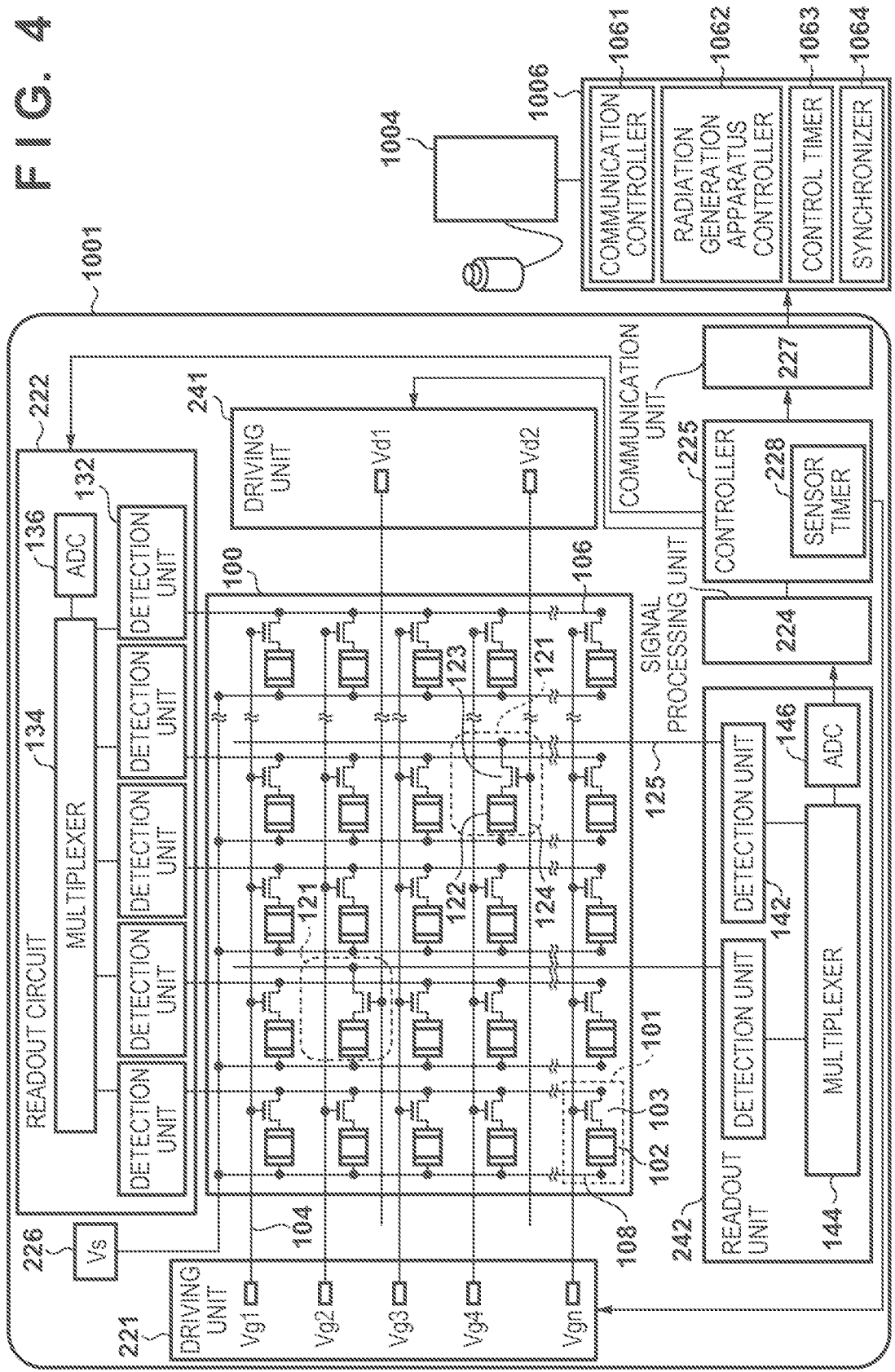
FIG. 4 is a view showing an arrangement example of the radiation imaging apparatus shown in FIG. 3.

FIG. 4 is a view showing an arrangement example of the radiation imaging apparatus 1001 according to this embodiment. The radiation imaging apparatus 1001 includes a plurality of pixels arranged in an imaging region 100 so as to form a plurality of rows and a plurality of columns. The plurality of pixels include a plurality of pixels 101 used to acquire a radiation image based on detected radiation and include a dose detection pixel 121 (to also be referred to as a detection unit) that detects the dose of radiation emitted from the radiation source 1003. The pixel 101 includes a conversion element 102 that converts radiation into an electrical signal and includes a switch 103 arranged between a column signal line 106 and the conversion element 102. Similar to the pixel 101, the dose detection pixel 121 includes a conversion element 122 that converts radiation into an electrical signal and includes a switch 123 arranged between a detection signal line 125 and the conversion element 122.

Each of the conversion element 102 and the conversion element 122 can include a scintillator that converts radiation into light and a photoelectric conversion element that converts light into an electrical signal. For example, the scintillator may be formed in a sheet shape so as to cover the imaging region 100, and the scintillator may be shared by the plurality of pixels 101 and 121. Each of the conversion element 102 and the conversion element 122 may be a conversion element that directly converts radiation into an electrical signal.

Each of the switch 103 and the switch 123 may be, for example, a thin film transistor (TFT) with an active region formed by a semiconductor, such as amorphous silicon or polysilicon. In this embodiment, a TFT using polysilicon is used as each of the switches 103 and 123.

The radiation imaging apparatus 1001 includes a plurality of the column signal lines 106 and a plurality of driving lines 104. Each column signal line 106 can correspond to one of the plurality of columns in the imaging region 100. Each driving line 104 corresponds to one of the plurality of rows in the imaging region 100. Here, "column" indicates the vertical direction in FIG. 4, and "row" indicates the horizontal direction in FIG. 4. A driving signal is supplied to each driving line 104 by a driving unit 221.

One electrode of the main electrodes of the conversion element 102 is connected to one electrode of the main electrodes of the switch 103, and the other electrode of the conversion element 102 is connected to a bias line 108. Here, each bias line 108 extends in the column direction, and is commonly connected to the other electrodes of the multiple conversion elements 102 arranged in the column direction. A bias voltage Vs is supplied to the bias line 108 from a power supply unit 226. The other electrodes of the main electrodes of the switches 103 of the multiple pixels 101 forming one column are connected to one corresponding column signal line 106. The control electrodes of the switches 103 of the multiple pixels 101 forming one row are connected to one corresponding driving line 104.

The plurality of column signal lines 106 are connected to a readout unit 222. Here, the readout unit 222 can include a plurality of detection units 132, a multiplexer 134, and an analog/digital (AD) converter 136. Each of the plurality of column signal lines 106 is connected to a corresponding one of the plurality of detection units 132 of the readout unit 222. One column signal line 106 corresponds to one detection unit 132. The detection unit 132 includes, for example, a differential amplifier. The multiplexer 134 selects the plurality of detection units 132 in a predetermined order, and supplies, to the AD converter 136, a signal output from the selected detection unit 132. The AD converter 136 converts the supplied analog signal into a digital signal and outputs the digital signal.

One electrode of the main electrodes of the conversion element 122 is connected to one electrode of the main electrodes of the switch 123, and the other electrode of the conversion element 122 is connected to the bias line 108. The other main electrode of the main electrodes of the switch 123 is electrically connected to the detection signal line 125. The control electrode of the switch 123 is electrically connected to a driving line 124. The radiation imaging apparatus 1001 can include a plurality of detection signal lines 125. One detection signal line 125 can be connected to one or multiple dose detection pixels 121. The driving line 124 is driven by a driving unit 241. One driving line 124 can be connected to one or multiple dose detection pixels 121.

Each detection signal line 125 is connected to a readout unit 242 (which may also be referred to as an AEC readout unit). The readout unit 242 can include a plurality of detection units 142, a multiplexer 144, and an AD converter 146. Each of the plurality of detection signal lines 125 can be connected to a corresponding one of the plurality of detection units 142 of the readout unit 242. One detection signal line 125 corresponds to one detection unit 142. Each detection unit 142 includes, for example, a differential amplifier. The multiplexer 144 selects the plurality of detection units 142 in a predetermined order, and supplies, to the AD converter 146, a signal output from the selected detection unit 142. The AD converter 146 converts the supplied signal into a digital signal and outputs the digital signal.

The output of the AD convertor 146 of the readout unit 242 is supplied to a signal processing unit 224 and processed by the signal processing unit 224. Based on the output of the AD convertor 146 of the readout unit 242, the signal processing unit 224 outputs information of the radiation applied to the radiation imaging apparatus 1001.

Based on the electrical signal generated by the pixel 121 in accordance with the irradiated radiation, the signal processing unit 224 acquires information of the dose of radiation entering the pixel 121. The signal processing unit 224 may generate a signal by performing digital signal processing to the detection result of the pixel 121. For example, the signal processing unit 224 may be configured to, based on the generated signal, detect the start of radiation irradiation with respect to the radiation imaging apparatus 1001, or calculate the irradiation dose and integrated irradiation amount (arrival dose) of radiation. Also, the signal processing unit 224 may transmit, to the radiation control apparatus 1006, the acquired information of the dose of radiation entering the pixel 121, and the radiation control apparatus 1006 may acquire the irradiation dose and integrated irradiation amount (arrival dose) of radiation.

A controller 225 controls the operation of each of the driving unit 221, the driving unit 241, and the readout units 222 and 242. Further, the controller 225 is provided with a sensor timer 228. The sensor timer 228 measures the time at which the signal processing unit 224 detected the dose entering the pixel 121 of the radiation imaging apparatus 1001. The controller 225 acquires, from the signal processing unit 224, the information of the dose of radiation entering the pixel 121, and acquires the information of the time from the sensor timer 228. Here, let $X_i$ be the information of the dose, and let $T_i$ be the information of the time. The information including a combination of the dose $X_i$ and the time $T_i$ is referred to as dose information $D_i$. The controller 225 generates the dose information $D_i(T_i, X_i)$ including the dose Xi entering the pixel 121 of the radiation imaging apparatus 1001 and the time Ti at which the dose Xi was detected.

The radiation imaging apparatus 1001 includes a communication unit 227 used to communicate with the radiation control apparatus 1006 and the control apparatus 1002. The communication unit 227 may include two communication units of a wired communication unit and a wireless communication unit. The communication unit 227 can transmit, to the radiation control apparatus 1006 and the control apparatus 1002, the information output from the controller 225 by using the wired communication unit or the wireless communication unit. For example, the communication unit 227 outputs the dose information Di(Ti, Xi) generated by the controller 225 to the radiation control apparatus 1006. The controller 225 acquires, from the signal processing unit 224, the information of the detected dose Xi at regular intervals, generates the dose information Di(Ti, Xi), and outputs the generated dose information Di to the radiation control apparatus 1006 via the communication unit 227.

A generation controller 1062 of the radiation control apparatus 1006 appends, to the received dose information Di(Ti, Xi), a time Ti' at which the radiation control apparatus acquired the dose information, thereby generating dose information Di' (Ti, Ti', Xi). In order to generates the dose information Di', the radiation control apparatus 1006 includes a control timer 1063. The control timer 1063 measures information of the time in the radiation control apparatus 1006. The radiation control apparatus 1006 can also include a synchronizer 1064 used to synchronize the information of the time of the control timer 1063 and the information of the time of the sensor timer 228 of the radiation imaging apparatus 1001. The synchronizer 1064 may set the time of the sensor timer 228 of the radiation imaging apparatus 1001 based on the information of the time of the control timer 1063 of the radiation control apparatus 1006. The synchronizer 1064 may be configured to be capable of communication of the information of the time with the communication unit 227 of the radiation imaging apparatus 1001 by wireless communication or wired communication. In this embodiment, the synchronizer 1064 performs wireless communication with the communication unit 227 of the radiation imaging apparatus 1001.

The controller 225 of the radiation imaging apparatus 1001 monitors the reception state of the communication 227 and, if the timer information is received, sets the time of the sensor timer 228 based on the received timer information. When the time of the sensor timer 228 is set based on the timer information, the time of the control timer 1063 of the radiation control apparatus 1006 and the time of the sensor timer 228 are synchronized with each other. The synchronizer 1064 synchronizes the time of the control timer 1063 of the radiation control apparatus 1006 and the time of the sensor timer 228 of the radiation imaging apparatus 1001 before radiation is emitted and radiation image capturing is started in the radiation imaging apparatus 1001. Here, synchronizing the times is not limited to setting the time of the control timer 1063 and the time of the sensor timer 228 to the same time, and there may be a predetermined difference between the two times. As long as the delay between the above-described time Ti and time Ti' can be acquired, synchronization between the time of the control timer 1063 and the time of the sensor timer 228 may take any form. By executing synchronization of the times prior to radiation image capturing in the radiation imaging apparatus 1001, it is possible to suppress a relative time shift between the time of the sensor timer 228 of the radiation imaging apparatus 1001 and the time of the control timer 1063 of the radiation control apparatus 1006.

The arrangement example has been described in FIG. 1 in which the radiation control apparatus 1006 includes the synchronizer 1064, but the radiation imaging apparatus 1001 may include a synchronizer. Also, the synchronizer 1064 may be arranged in the radiation imaging system 1000 while being independent of the radiation control apparatus 1006 and the radiation imaging apparatus 1001. Any form can be employed as long as the time of the control timer 1063 of the radiation control apparatus 1006 and the time of the sensor timer 228 of the radiation imaging apparatus 1001 can be synchronized with each other.

Based on the dose information Di(Ti, Xi) including the dose Xi of radiation entering the pixel 121 and the time Ti at which the dose Xi was detected, the generation controller 1062 of the radiation control apparatus 1006 specifies the threshold time at which the arrival dose entering the radiation imaging apparatus 1001 (pixel 121) reaches a preset threshold dose. More specifically, based on the dose Xi and time Ti included in the dose information Di(Ti, Xi) output from the communication unit 227 of the radiation imaging apparatus 1001 and the time Ti' at which the radiation control apparatus 1006 received the dose information Di, the generation controller 1062 calculates a threshold time Te at which the arrival dose entering the radiation imaging apparatus 1001 reaches a threshold dose Y. Then, the generation controller 1062 of the radiation control apparatus 1006 controls the radiation source control apparatus 1004 to output an irradiation control signal such that the radiation source 1003 emits radiation until the time obtained by the control timer 1063 reaches the threshold time Te.

At this time, the communication between the radiation imaging apparatus 1001 and the radiation control apparatus 1006 may become unstable due to a change in environment of the wireless communication between the radiation imaging apparatus 1001 and the radiation control apparatus 1006. For example, there is a case in which a shift occurs between the time Ti of the dose information Di output from the radiation imaging apparatus 1001 and the time Ti' at which the radiation control apparatus 1006 acquired the dose information Di. In this case, the relationship between the threshold dose Y and the information of the arrival dose acquired from the actual dose information Di may become inappropriate. Therefore, the generation controller 1062 of the radiation control apparatus 1006 changes and corrects the threshold dose Y based on the difference between the time Ti included in the dose information Di and the time Ti' at which the radiation control apparatus 1006 acquired the dose information Di. With this, the generation controller 1062 of the radiation control apparatus 1006 can output the irradiation control signal to the radiation source control apparatus 1004 at an appropriate timing. That is, the controllability of radiation irradiation can be improved in the radiation imaging system 1000.

Figure 5:
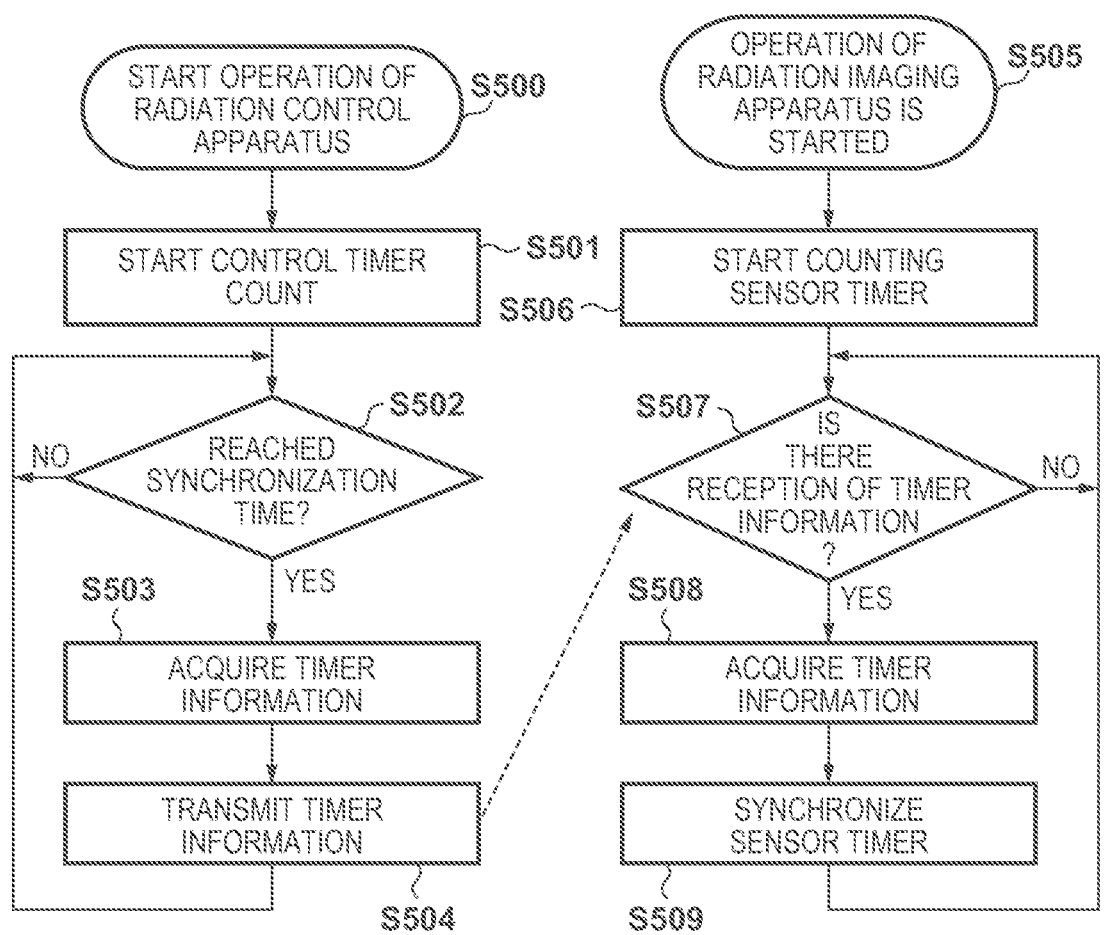
FIG. 5 is a flowchart illustrating an operation example of the radiation imaging system shown in FIG. 1.

Here, with reference to FIG. 5, the procedure of synchronization processing of synchronizing the time of the control timer 1063 of the radiation control apparatus 1006 and the time of the sensor timer 228 of the radiation imaging apparatus 1001 will be described as an operation procedure of the radiation imaging system 1000. When operation of the radiation control apparatus 1006 is started by a user operation or the like (step S500), the control timer 1063 of the radiation control apparatus 1006 starts to measure the time (starts counting) in step S501. Then, in step S502, synchronization time waiting processing is performed. The synchronization time is a time at which a predetermined time has elapsed since the control timer 1063 starts counting. The control timer 1063 of the radiation control apparatus 1006 measures the elapse time after the start of counting. If the elapse time has not reached the time (synchronization time) at which the predetermined time has elapsed after the start of counting (No in step S502), the radiation control apparatus 1006 waits until the elapse time reaches the synchronization time. If the elapse time reaches the synchronization time (Yes in step S502), the radiation control apparatus 1006 advances the process to step S503.

In step S503, the synchronizer 1064 of the radiation control apparatus 1006 acquires the timer information based on the time measured by the control timer 1063. The synchronizer 1064 acquires information of the time measured by the control timer 1063 and, in step S504, outputs the timer information (the information of the time of the control timer 1063) acquired from the control timer 1063 to the radiation imaging apparatus 1001 under the control of the communication controller 1061. Transmission processing of the timer information in step S504 is performed every time the synchronization time is reached, regardless of whether the timer information is received in the radiation imaging apparatus 1001.

Next, the operation in the radiation imaging apparatus 1001 will be described. When operation of the radiation imaging apparatus 1001 is started by a user operation or the like (step S505), the sensor timer 228 of the radiation imaging apparatus 1001 starts to measure the time (starts counting) in step S506. Then, in step S507, the controller 225 of the radiation imaging apparatus 1001 monitors whether the communication unit 227 receives the timer information, and waits in a state of waiting for reception of the timer information. If the timer information is not received (No in step S507), the controller 225 of the radiation imaging apparatus 1001 continues the waiting state. If the timer information is received (Yes in step S507), the controller 225 advances the process to step S508. In step S508, the controller 225 acquires the timer information received by the communication unit 227. When the timer information is acquired, in step S509, the controller 225 sets the time of the sensor timer 228 based on the acquired timer information. When the time of the sensor timer 228 is set based on the timer information, the time of the sensor timer 228 is synchronized with the time of the control timer 1063 of the radiation control apparatus 1006.

When the time of the sensor timer 228 is synchronized with the time of the control timer 1063 of the radiation control apparatus 1006 in step S509, the process returns to step S507, and the controller 225 waits in the state of waiting for reception of the timer information. Thereafter, if the timer information is similarly received (Yes in step S507), the controller 225 of the radiation imaging apparatus 1001 sets the time of the sensor timer 228 based on the timer information received by the communication unit 227 (step S509). With this, the time of the control timer 1063 of the radiation control apparatus 1006 and the time of the sensor timer 228 can be accurately synchronized with each other.

The control timer 1063 of the radiation control apparatus 1006 can start counting the operation time at the same time with power-on of the radiation control apparatus 1006 and can measure the time. The synchronizer 1064 acquires the timer information based on the time measured by the control timer 1063. The synchronizer 1064 may transmit the timer information to the radiation imaging apparatus 1001, for example, every several μs, as the synchronization time under the control of the communication controller 1061. The timing (synchronization time) at which the synchronizer 1064 transmits the timer information using the communication controller 1061 can be arbitrarily set.

The controller 225 of the radiation imaging apparatus 1001 transmits the dose information Di(Ti, Xi) to the radiation control apparatus 1006 via the communication unit 227, for example, every synchronization time. The generation controller 1062 of the radiation control apparatus 1006 can control output of an irradiation control signal to the radiation source control apparatus 1004 based on the arrival dose information Di(Ti, Xi) transmitted from the radiation imaging apparatus 1001.

Figures 6A, 6B:
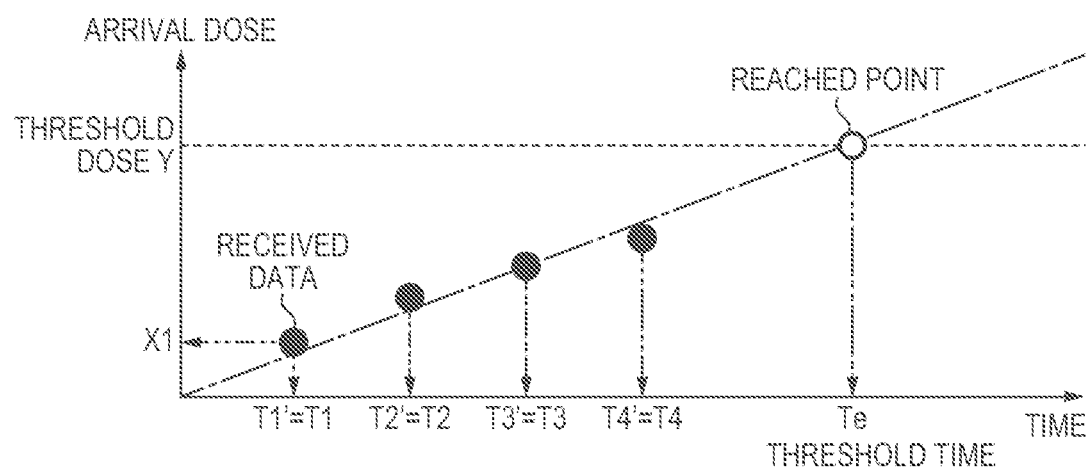
FIGS. 6A to 6C are a table and graphs showing an example of the radiation irradiation control of the radiation imaging system shown in FIG. 1.
Figure 6C:
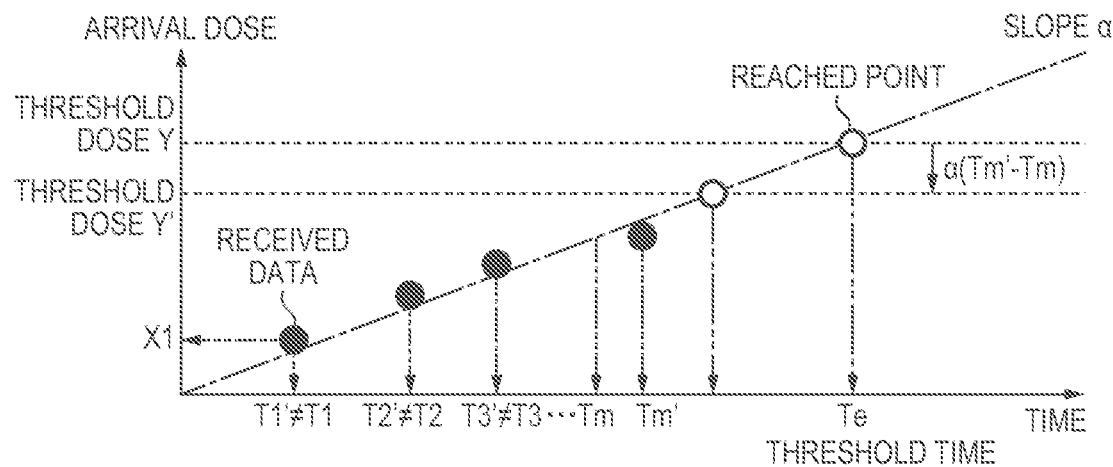

Next, with reference to FIGS. 6A to 6C, a correction method and radiation irradiation control in a case in which a shift (difference) between the time Ti of the dose information Di and the time Ti' at which the radiation control apparatus 1006 acquired the dose information Di occurs in the radiation control apparatus 1006 will be described.

The radiation imaging apparatus 1001 sequentially outputs the dose information Di(Ti, Xi) at a predetermined timing (for example, every synchronization time as described above), and the generation controller 1062 stores the dose information Di' (Ti, Ti', Xi) obtained by adding the acquirement time Ti' in a memory (not shown) in the radiation control apparatus 1006. The radiation imaging apparatus 1001 can output the dose information Di to the radiation control apparatus 1006 a plurality of times, and the radiation control apparatus 1006 can store a plurality of pieces of the dose information Di' in the memory. FIG. 6A is a table showing examples of pieces of dose information Di' (Ti, Ti', Xi) stored in the memory of the radiation control apparatus 1006. Each dose information Di' is stored in a state in which the time Ti at which the dose Xi was detected in the radiation imaging apparatus 1001 and the time Ti' at which the generation controller 1062 of the radiation control apparatus 1006 received the dose information Di are associated with the dose Xi (i=1, 2, ..., m). The generation controller 1062 of the radiation control apparatus 1006 also stores the threshold dose Y of the arrival dose in the memory. The threshold dose Y for stopping radiation irradiation can be arbitrarily set by the user, and can be changed in accordance with the imaging method, imaging portion, imaging condition, and the like.

Based on the dose information Di including the dose Xi of radiation entering the radiation imaging apparatus 1001 (pixel 121) and the time Ti, the generation controller 1062 of the radiation control apparatus 1006 can specify the threshold time Te which is the predicted time at which the arrival dose entering the radiation imaging apparatus 1001 reaches the preset threshold dose Y. As shown in FIG. 6B, straight-line approximation based on the least square method using a plurality of pieces of the dose information Di or the like can be used to specify the threshold time Te.

The generation controller 1062 of the radiation control apparatus 1006 can control radiation irradiation via the radiation source 1003 based on a comparison between the threshold dose Y and the dose information Di acquired after the threshold time Te is specified, and the threshold time Te. That is, if the arrival dose obtained from the dose information Di reaches the threshold dose Y or if the time of the control timer 1063 reaches the threshold time Te, the generation controller 1062 of the radiation control apparatus 1006 can control the radiation source 1003 to stop radiation irradiation.

Next, with reference to FIG. 6C, a case will be described in which, for example, the communication between the radiation imaging apparatus 1001 and the radiation control apparatus 1006 becomes unstable due to a change in wireless environment or the like, and a shift occurs between the time Ti of the dose information Di output from the radiation imaging apparatus 1001 and the time Ti' at which the radiation control apparatus 1006 acquired the dose information Di. If the difference between the time Ti of the dose information Di output from the radiation imaging apparatus 1001 and the time Ti' at which the radiation control apparatus 1006 acquired the dose information Di exceeds a predetermined threshold value, the generation controller 1062 of the radiation control apparatus 1006 changes the threshold dose Y. More specifically, if the difference (delay time (Tm'−Tm)) between a time Tm of dose information Dm output from the radiation imaging apparatus 1001 acquired after the threshold time Te is specified (for example, after the threshold time Te is first specified) and a time Tm' at which the radiation control apparatus 1006 acquired the dose information Dm becomes equal to or larger than a predetermined time, a threshold change amount α(Tm'−Tm) is calculated from the delay time (Tm'−Tm) and a slope α of the approximate straight line used when calculating the threshold dose Y. Then, {Y−α(Tm'−Tm)} obtained by subtracting the threshold change amount α(Tm'−Tm) from the set threshold dose Y is set as a new threshold dose Y'. If the arrival dose obtained from the dose information Di reaches the threshold dose Y' or if the time of the control timer 1063 reaches the threshold time Te, the generation controller 1062 of the radiation control apparatus 1006 changes a signal output to the radiation source control apparatus 1004 so as to switch from the radiation irradiation state to the irradiation stop state.

A radiation image capturing method performed in the radiation imaging system 1000 includes, for example, processing steps described below. First, the dose Xi of radiation emitted from the radiation source 1003 is detected using the pixel 121 of the radiation imaging apparatus 1001. The dose information Di including the dose Xi and the time Ti at which the dose Xi was detected is transmitted to the radiation control apparatus 1006. The generation controller 1062 of the radiation control apparatus 1006 acquires, based on the transmitted dose information Di, the threshold time Te at which the arrival dose (integrated dose) entering the radiation imaging apparatus 1001 reaches the threshold dose Y. Based on a comparison between the arrival dose entering the radiation imaging apparatus 1001 and the threshold dose Y or a comparison between the time measured by the control timer 1063 and the threshold time Te, the generation controller 1062 controls the radiation emission from the radiation source 1003.

Here, the delay time is not limited to a delay caused by the communication between the radiation imaging apparatus 1001 and the radiation control apparatus 1006 as described above. For example, there is a possibility that when a delay occurs before the dose information Di is output, for example, a load is applied on the operation of the radiation imaging apparatus 1001, during a period after the dose information Di is generated in the radiation imaging apparatus 1001 and before the dose information Di is output via the communication unit 227. Similarly, there is a possibility that a delay occurs after the dose information Di is received in the radiation control apparatus 1006 and before the dose information Di' is generated in the generation controller 1062. In consideration of the possibilities described above, the threshold value Y may be changed if the difference (delay time (Tm'−Tm)) between the time Tm of the dose information Dm output from the radiation imaging apparatus 1001 and the time Tm' at which the radiation control apparatus 1006 acquired the dose information Dm exceeds a predetermined threshold.

Each of the sensor timer 228 and the control timer 1063 used in this embodiment is not limited to a counter that counts the time, and may be configured to measure the actual time. In addition, in this embodiment, it has been described that the radiation control apparatus 1006 and the control apparatus 1002 are independent apparatuses, but the radiation control apparatus 1006 and the control apparatus 1002 may be integrally formed.

Figure 7:
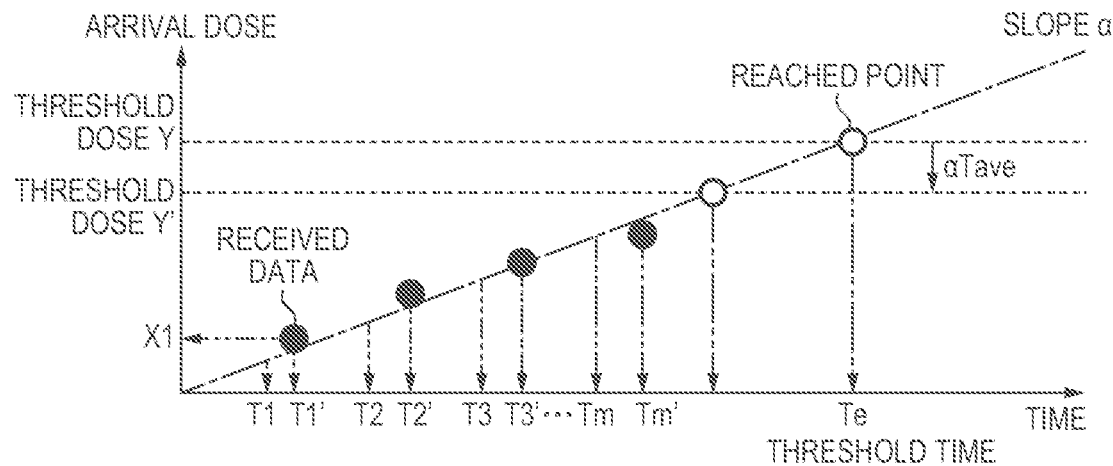
FIG. 7 is a graph showing another example of the radiation irradiation control of the radiation imaging system shown in FIG. 1.

Next, a modification of the method of changing the threshold dose Y will be described. In the description with reference to FIGS. 6A to 6C, it has been described that the radiation control apparatus 1006 changes the threshold dose Y based on the difference between the time Tm included in one piece of dose information Dm among the plurality of pieces of the dose information Di and the time Tm' at which the radiation control apparatus 1006 acquired the one piece of dose information Dm. However, the radiation control apparatus 1006 may change the threshold dose Y based on the differences between the times Ti included in two or more pieces of dose information Di among the plurality of pieces of the dose information Di and the times Ti' at which the radiation control apparatus 1006 acquired the two or more pieces of dose information Di, respectively. That is, the threshold does Y may be corrected using the average time of the delay times of multiple pieces of dose information Di. With reference to FIG. 7, a case of using the average time of delay times of multiple pieces of dose information Di' will be described.

Assume that a predetermined difference (delay time) or more occurs between the acquisition time Ti of the dose information Di output from the radiation imaging apparatus 1001 and the time Ti' at which the radiation control apparatus 1006 acquired the dose information Di. In this case, the generation controller 1062 of the radiation control apparatus 1006 calculates an average delay time Tave from pieces of information of the times Ti included in the respective pieces of dose information Di and the times Ti' at which the radiation control apparatus 1006 acquired the respective pieces of dose information Di. For example, Tave can be expressed as:

$$\text{Tave} = \{(T1'-T1)+(T2'-T2)+(T3'-T3)+ \ldots +(Tm'-Tm)\}/m \quad (1)$$

Further, the generation controller 1062 calculates a threshold change amount αTave from the slope α of the approximate straight line and the average delay time Tave. Then, (Y−αTave) obtained by subtracting the threshold change amount from the set threshold dose Y is stored as the new threshold dose Y' in the memory.

In this embodiment, all pieces of information from the first dose information D1(T1, T1', X1) to the latest dose information Dm(Tm, Tm', Xm) are used to calculate the average delay time Tave, but the information to be used may be arbitrarily selected. That is, an arbitrary number of data before the timing at which the predetermined delay time or more occurs may be used. Also, a predetermined delay time for calculating the average delay time Tave is set, and only the information with which the predetermined delay time or more occurs may be used.

Figure 8A:
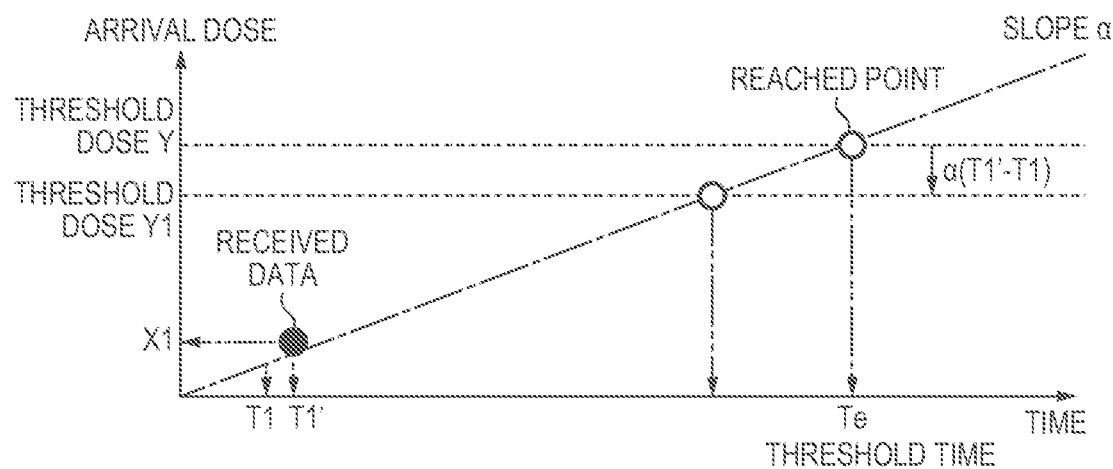
FIGS. 8A to 8C are graphs showing still another example of the radiation irradiation control of the radiation imaging system shown in FIG. 1.
Figure 8B:
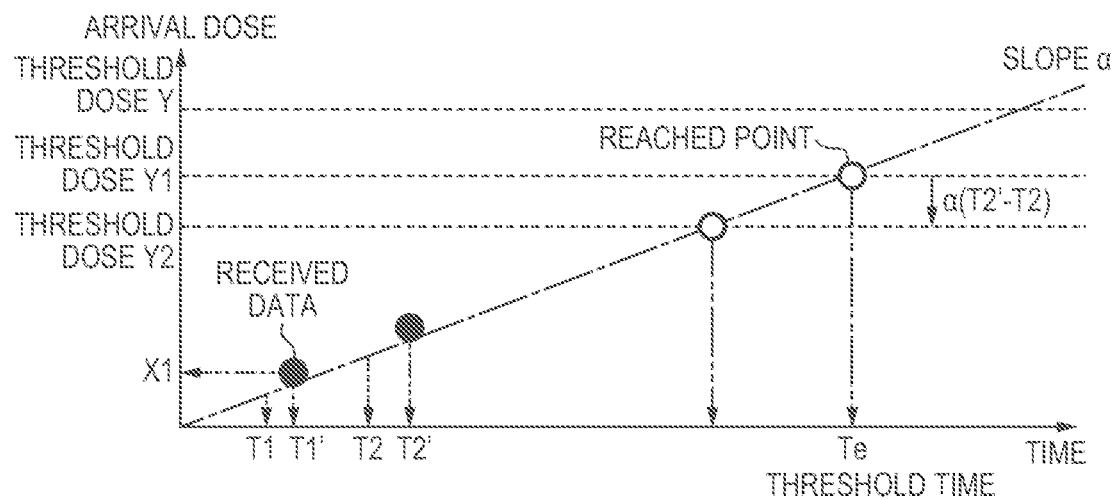
Figure 8C:
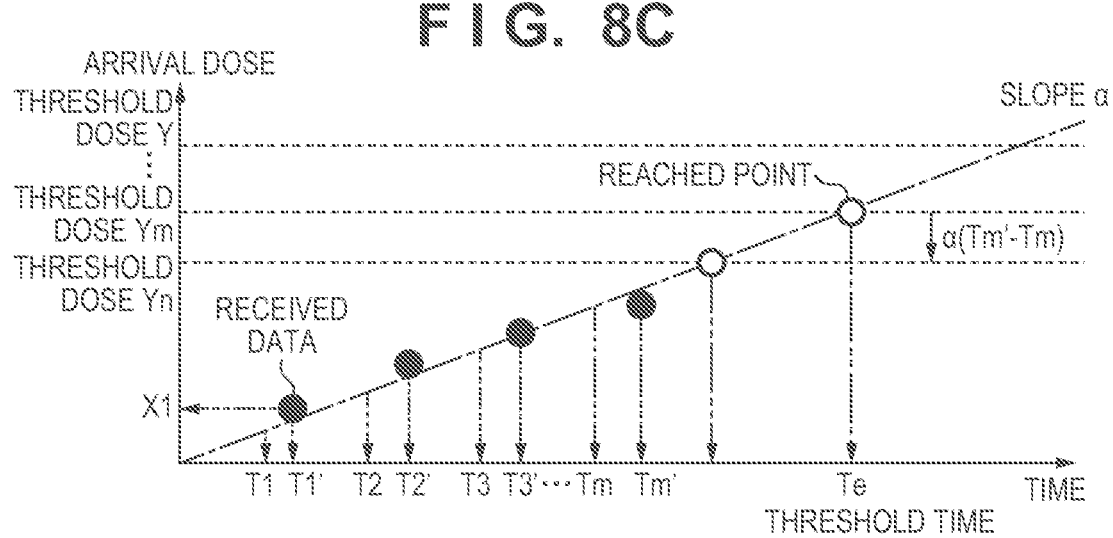

Still another example of the method of changing the threshold dose Y will be described. In the embodiment described above, the threshold dose Y is corrected if the predetermined delay time or more occurs, but some embodiments are not limited to this. For example, the radiation control apparatus 1006 may change the threshold dose Y every time the dose information Di is acquired. With reference to FIGS. 8A to 8C, a case will be described in which the radiation control apparatus 1006 changes the threshold dose Y every time the dose information Di is received.

As shown in FIG. 8A, after the first does information D1 from the radiation imaging apparatus 1001 is acquired, the generation controller 1062 of the radiation control apparatus 1006 specifies the threshold dose Y using the dose X1, the time T1, and the time T1' at which the radiation control apparatus 1006 acquired the dose information D1. Further, the generation controller 1062 of the radiation control apparatus 1006 calculates a threshold change amount $\alpha(T1'-T1)$ from the slope $\alpha$ of the approximate straight line used upon the specification and a delay time $(T1'-T1)$. Then, $\{Y-\alpha(T1'-T1)\}$ obtained by subtracting the threshold change amount from the threshold dose Y is stored as a new threshold dose Y1 in the memory.

Then, as shown in FIG. 8B, after next dose information D2 from the radiation imaging apparatus 1001 is acquired, the generation controller 1062 of the radiation control apparatus 1006 recorrects the threshold dose again using a dose X2, a time T2, and a time T2' at which the radiation control apparatus 1006 acquired the dose information D2. More specifically, a threshold change amount $\alpha(T2'-T2)$ is calculated from the slope $\alpha$ of the approximate straight line and a delay time $(T2'-T2)$. Then, $\{Y1-\alpha(T2'-T2)\}$ obtained by subtracting the threshold change amount from the threshold dose Y1 is stored as a new threshold dose Y2 in the memory. That is, as shown in FIG. 8C, a threshold dose Yn at the time when nth dose information Dn was acquired is expressed as $Yn=Ym-\alpha(Tn'-Tn)$ (where $m=n-1$).

In this embodiment, the method of correcting the threshold dose Y every time the radiation control apparatus 1006 acquires the dose information Di has been described. However, the correction timing may be an arbitrary timing. For example, the radiation control apparatus 1006 may change the threshold dose Y based on the dose information Di, among the plurality of pieces of the dose information Di, acquired at a preset timing. Also, for example, the radiation control apparatus 1006 may change the threshold dose Y based on the dose information Di, among the plurality of pieces of the dose information Di, acquired at the timing at which a predetermined period has elapsed since the threshold dose Y was last changed.

Figure 9:
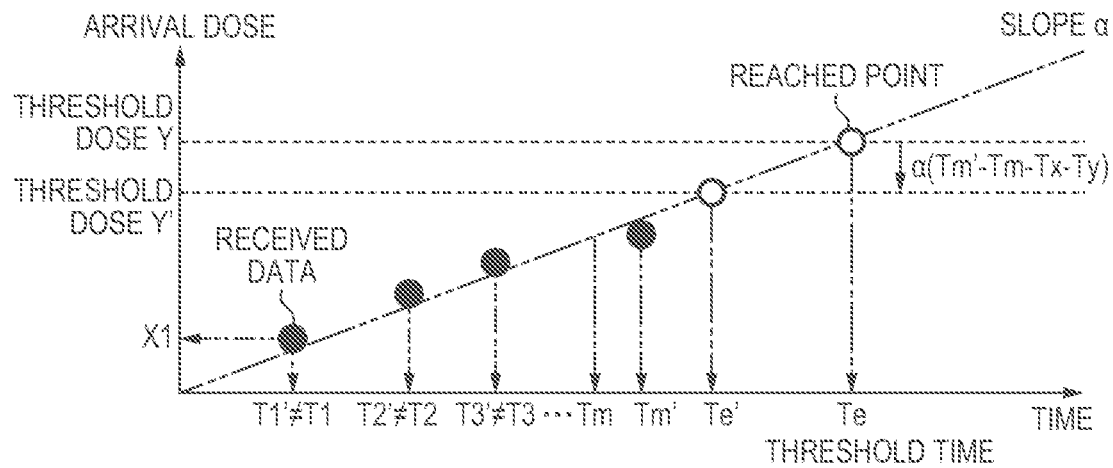
FIG. 9 is a graph showing still another example of the radiation irradiation control of the radiation imaging system shown in FIG. 1.

When changing the threshold dose Y, the period from when the generation controller 1062 changes the irradiation control signal output to the generation source control apparatus 1004 so as to switch from the radiation irradiation state to the irradiation stop state to when the radiation irradiation from the radiation source 1003 is actually stopped may be taken into consideration. As shown in FIG. 1, the radiation control apparatus 1006, the radiation source control apparatus 1004, and the radiation source 1003 are wired-connected using a cable or the like, and transmit/receive signals. That is, the radiation control apparatus 1006 and the radiation source 1003 are configured to be capable of communication by wired communication. In this case, a time Tx from when the generation controller 1062 transmits a signal to the radiation source control apparatus 1004 so as to switch from the radiation irradiation state to the irradiation stop state to when the radiation source control apparatus 1004 receives the signal can be a unique value for each radiation imaging system 1000. Further, a time Ty from when the radiation source control apparatus 1004 receives the signal to when the radiation source 1003 stops radiation irradiation can be a unique value for each radiation imaging system 1000, each imaging procedure, and each imaging condition. That is, a time $(Tx+Ty)$ from when the radiation control apparatus 1006 transmits the signal for causing the radiation source 1003 to stop radiation irradiation based on the dose information Di and the threshold time Te as described above to when the radiation source 1003 stops radiation irradiation can be a unique value according to the radiation imaging system 1000, the imaging procedure, and the imaging condition. Therefore, as shown in FIG. 9, the radiation control apparatus 1006 may change at least one of the threshold dose Y or the threshold time Te based on the time $(Tx+Ty)$ from when the signal to stop radiation irradiation is transmitted to when the radiation source 1003 stops radiation irradiation. By taking the time $(Tx+Ty)$ into consideration when correcting the threshold dose Y, it is possible to further suppress excessive radiation irradiation.

More specifically, first, it is necessary to acquire, before imaging, the time $(Tx+Ty)$ from when the generation controller 1062 of the radiation control apparatus 1006 changes the irradiation control signal transmitted to the radiation source control apparatus 1004 to when the radiation irradiation from the radiation source 1003 is actually stopped. The time $(Tx+Ty)$ may be actually measured at the time of installation of the radiation imaging system 1000, or may be measured in advance before shipping from the factory or the like. Also, the time $(Tx+Ty)$ may be registered in the control apparatus 1002 or the like as a database in advance, and the database may be referred to.

Then, if the predetermined delay time or more occurs between the time Ti of the dose information Di output from the radiation imaging apparatus 1001 and the time Ti' at which the radiation control apparatus 1006 acquired the dose information Di, the generation controller 1062 changes the threshold dose Y. As has been described above, a threshold change amount $\alpha(Tm'-Tm-Tx-Ty)$ is calculated from the delay time $(Tm'-Tm)$ and the unique time $(Tx-Ty)$ according to the radiation imaging system 1000, the imaging procedure, the imaging condition, and the like in addition to the slope $\alpha$ of the approximation straight line used when specifying the threshold dose Y. $\{Y-\alpha(Tm'-Tm-Tx-Ty)\}$ obtained by subtracting the threshold change amount from the set threshold dose Y is stored as the new threshold dose Y' in the memory and set. Further, the generation controller 1062 calculates a threshold time Te' $(Te'=Te-Tx-Ty)$ as a predicted time. In this manner, by taking the time from when the radiation control apparatus 1006 determines to stop radiation irradiation to when the radiation source 1003 stops the radiation irradiation into consideration, the accuracy of radiation irradiation is further improved in the radiation imaging system 1000.

Other Embodiments

Some embodiment(s) of the present disclosure can also be realized by a computer of a system or apparatus that reads out and executes computer-executable instructions (e.g., one or more programs) recorded on a storage medium (which may also be referred to more fully as anon-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has described exemplary embodiments, it is to be understood that some embodiments are not limited to the disclosed exemplary embodiments. The scope of the following claims is to be accorded the broadest interpretation so as to encompass all such modifications and equivalent structures and functions.

This application claims priority to Japanese Patent Application No. 2021-172654, which was filed on Oct. 21, 2021 and which is hereby incorporated by reference herein in its entirety.

What is claimed is:

1. A radiation imaging system comprising:
a radiation imaging apparatus configured to detect radiation emitted from a radiation source; and
a radiation control apparatus configured to control the radiation source, wherein
the radiation imaging apparatus is configured to output dose information, which includes a dose of radiation entering the radiation imaging apparatus and a time at which the dose was detected, to the radiation control apparatus a plurality of times, and
the radiation control apparatus is configured to
set a threshold dose based on a difference between a time included in the dose information from the radiation imaging apparatus and a time at which the radiation control apparatus received the dose information, and
control the radiation source to stop radiation irradiation based on the threshold dose.

2. The system according to claim 1, wherein
the radiation control apparatus is configured to specify, based on the dose information, a threshold time at which an arrival dose entering the radiation imaging apparatus reaches the threshold dose.

3. The system according to claim 1, wherein
the radiation control apparatus is configured to set the threshold dose based on a difference between a time included in one piece of dose information among a plurality of pieces of the dose information and a time at which the radiation control apparatus acquired the one piece of dose information.

4. The system according to claim 1, wherein
the radiation control apparatus is configured to set the threshold dose based on differences between times included in two or more pieces of dose information among a plurality of pieces of the dose information and times at which the radiation control apparatus acquired the two or more pieces of dose information, respectively.

5. The system according to claim 1, wherein
if the difference exceeds a predetermined threshold, the radiation control apparatus is configured to set the threshold dose.

6. The system according to claim 1, wherein
the radiation control apparatus is configured to set the threshold dose based on dose information, among a plurality of pieces of the dose information, acquired at a preset timing.

7. The system according to claim 1, wherein
the radiation control apparatus is configured to set the threshold dose based on dose information, among a plurality of pieces of the dose information, acquired at a timing at which a predetermined period has elapsed since the threshold dose was last changed.

8. The system according to claim 2, wherein
if the arrival dose reaches the threshold dose or if a time reaches the threshold time, the radiation control apparatus is configured to control the radiation source to stop radiation irradiation.

9. The system according to claim 2, wherein
based on the dose information and the threshold time, the radiation control apparatus is configured to transmit a signal which causes the radiation source to stop radiation irradiation.

10. The system according to claim 9, wherein
based on a time from when the signal is transmitted to when the radiation source stops radiation irradiation, the radiation control apparatus is configured to set at least one of the threshold dose or the threshold time.

11. The system according to claim 10, wherein
the radiation control apparatus and the radiation source are configured to be capable of communication by wired communication.

12. The system according to claim 1, wherein
the radiation imaging apparatus and the radiation control apparatus are configured to be capable of communication by wireless communication.

13. The system according to claim 1, further comprising
a synchronizer configured to synchronize a time of the radiation imaging apparatus and a time of the radiation control apparatus.

14. The system according to claim 13, wherein
the synchronizer is configured to synchronize the time of the radiation imaging apparatus and the time of the radiation control apparatus by wired communication or wireless communication.

15. The system according to claim 13, wherein
the synchronizer is configured to synchronize the time of the radiation imaging apparatus and the time of the radiation control apparatus before radiation is emitted.

16. A radiation control apparatus that controls a radiation source configured to emit radiation to a radiation imaging apparatus, the radiation control apparatus comprising:
one or more memories; and
one or more processors that are configured to cooperate with the one or more memories to
set a threshold dose based on a difference between a time included in dose information from the radiation imaging apparatus and a time at which the radiation control apparatus received the dose information, and
control the radiation source to stop radiation irradiation based on the threshold dose.

17. A control method of a radiation imaging system comprising a radiation imaging apparatus configured to detect radiation emitted from a radiation source, and a radiation control apparatus configured to control the radiation source, the method comprising:
causing the radiation imaging apparatus to output dose information, which includes a dose of radiation entering the radiation imaging apparatus and a time at which the dose was detected, to the radiation control apparatus;

causing the radiation control apparatus to set a threshold dose based on a difference between a time included in the dose information from the radiation imaging apparatus and a time at which the radiation control apparatus received the dose information; and causing the radiation control apparatus to control the radiation source to stop radiation irradiation based on the threshold dose.

18. A control method of a radiation control apparatus that controls a radiation source configured to emit radiation to a radiation imaging apparatus, the method comprising:

setting a threshold dose based on a difference between a time included in the dose information from the radiation imaging apparatus and a time at which the radiation control apparatus recived the dose information; and controlling the radiation source to stop radiation irradiation based on the threshold dose.

19. A non-transitory computer-readable storage medium storing a program for causing a computer to execute a control method of a radiation imaging system comprising a radiation imaging apparatus configured to detect radiation emitted from a radiation source, and a radiation control apparatus configured to control the radiation source, the method comprising:

causing the radiation imaging apparatus to output dose information, which includes a dose of radiation entering the radiation imaging apparatus and a time at which the dose was detected, to the radiation control apparatus;

causing the radiation control apparatus to set a threshold dose based on a difference between a time included in the dose information from the radiation imaging apparatus and a time at which the radiation control apparatus received the dose information; and causing the radiation control apparatus to control the radiation source to stop radiation irradiation based on the threshold dose.

20. A non-transitory computer-readable storage medium storing a program for causing a computer to execute a control method of a radiation control apparatus that controls a radiation source configured to emit radiation to a radiation imaging apparatus, the method comprising:

setting a threshold dose based on a difference between a time included in dose information from the radiation imaging apparatus and a time at which the radiation control apparatus recived the dose information; and controlling the radiation source to stop radiation irradiation based on the threshold dose.

* * * * *